US 7,439,289 B2

(12) United States Patent
Durairaj et al.

(10) Patent No.: US 7,439,289 B2
(45) Date of Patent: Oct. 21, 2008

(54) BENZOYLRESORCINOL-BASED PHOSPHATE ESTER COMPOUNDS AS FLAME RETARDANTS

(75) Inventors: Raj B. Durairaj, Monroeville, PA (US); Gary A. Jesionowski, Pittsburgh, PA (US)

(73) Assignee: Indspec Chemical Corporation, Pittsburgh, PA (US)

( * ) Notice: Subject to any disclaimer, the term of this patent is extended or adjusted under 35 U.S.C. 154(b) by 470 days.

(21) Appl. No.: 11/233,537

(22) Filed: Sep. 21, 2005

(65) Prior Publication Data
US 2006/0063865 A1     Mar. 23, 2006

Related U.S. Application Data

(60) Provisional application No. 60/611,940, filed on Sep. 22, 2004.

(51) Int. Cl.
*C08K 5/521* (2006.01)
(52) U.S. Cl. .................. 524/140; 524/141; 558/71; 558/86; 558/90; 558/208; 558/210
(58) Field of Classification Search ................. 524/140, 524/141; 558/71, 86, 90, 208, 210
See application file for complete search history.

(56) References Cited

U.S. PATENT DOCUMENTS

| 3,686,367 | A | * | 8/1972 | Cowling ............ 558/86 |
| 5,204,394 | A | | 4/1993 | Gosens et al. |
| 5,418,317 | A | | 5/1995 | Raymond |
| 5,602,201 | A | | 2/1997 | Fujiguchi et al. |
| 6,204,313 | B1 | | 3/2001 | Bastiaens et al. |
| 6,583,256 | B2 | | 6/2003 | Vollenberg et al. |

| 2006/0014863 | A1 | * | 1/2006 | Lim et al. ............ 524/115 |

FOREIGN PATENT DOCUMENTS

| EP | 0 509 506 | 10/1992 |
| EP | 0509506 | A2 | 10/1992 |
| JP | 63-210184 | 8/1988 |
| JP | 2002-138283 | 5/2002 |

OTHER PUBLICATIONS

Raj Durairaj, "Flame Retardant" in "Resorcinol: Chemistry, Technology and Applications," Springer Verlag Publisher, Chapter 8.2, pp. 592-631 (2005).
English abstract of B2, May 14, 2002.
Notification of Transmittal of the International Search Report of PCT/US05/34409, mailed on Jan. 25, 2008.
International Search Report of PCT/US05/34409, mailed on Jan. 25, 2008.
Written Opinion of the International Search Report of PCT/US05/34409, mailed on Jan. 25, 2008.

* cited by examiner

*Primary Examiner*—Peter Szekely
(74) *Attorney, Agent, or Firm*—Jones Day; Benjamin Bai; Kam Law

(57) ABSTRACT

Benzoylresorcinol-based phosphate esters are obtained by reacting a benzoylresorcinol compound with a chlorophosphate. The benzoylresorcinol-based phosphate esters can function as flame retardants and/or UV stabilizers for polycarbonates (PC), poly(phenylene oxide) (PPO), polyesters (e.g., PET and PBT), polycarbonate and acrylonitrile-butadiene-styrene terpolymer (PC/ABS) blends, poly(phenylene oxide) and high-impact polystyrene (PPO/HIPS) blends and other polymers. The benzoylresorcinol-based phosphate ester flame retardants may possess enhanced thermal stability compared to resorcinol based phosphate ester (RDP). Synthetic procedures and applications of the benzoylresorcinol-based phosphate esters compounds are provided.

25 Claims, No Drawings

BENZOYLRESORCINOL-BASED PHOSPHATE ESTER COMPOUNDS AS FLAME RETARDANTS

PRIOR RELATED APPLICATIONS

This application claims the benefit under 35 U.S.C. § 120 of U.S. Provisional Patent Application Ser. No. 60/611,940, filed Sep. 22, 2004, which is incorporated herein by reference in its entirety.

FIELD OF THE INVENTION

The invention relates to flame retardants comprising phosphate ester compounds, methods for their synthesis and applications thereof, especially their applications as flame retardants in compositions or articles comprising polymers.

BACKGROUND OF THE INVENTION

Polymers such as plastics, elastomers, and thermosets are used in large volumes in a wide range of applications such as walls, ceilings, furniture, floor coverings, fabrics, electronics, vehicles and electrical appliances. Because most polymers are flammable, fire safety is important in each of these applications. Generally, fire safety of polymers can be improved by incorporated therein flame retardants. Flame retardants consist of compounds added to a material to improve the material's ability to withstand fire and heat or to resist combustion. Flame retardants can function in a variety of ways to reduce the risk of fire hazard. In one way, they can raise the ignition temperature. In the other ways, they can reduce the rate of burning, flame spread, or the generation of toxic gases and smoke. Phosphorus flame retardants can reduce flammability of the polymer and reduce the generation of toxic gases and smoke.

There are many different kinds of flame retardants which include alumina trihydrate, magnesium hydroxide, halogenated compounds (e.g., chlorinated, fluorinated and brominated compounds), phosphorus compounds (e.g., phosphate esters), antimony oxide, melamine derivatives, and boric acid and other boron compounds. The worldwide sale of flame retardants was 2.35 billion pounds in 2003. It is predicted that the worldwide sale of flame retardants will increase to 2.82 billion pounds in 2008. Among all flame retardants, the two most common kinds are phosphorus flame retardants and halogenated flame retardants. Because of environmental and health concerns over halogenated flame retardants, many parts of Europe are considering bans on some specific halogenated flame retardants. Therefore, the trend is to restrain the use of the halogenated flame retardants and to migrate to other flame retardants such as phosphorus flame retardants. Some examples of phosphorus flame retardants currently in the market includes phosphate ester type flame retardants such as resorcinol bis(diphenyl phosphate) (RDP), bisphenol A bis(diphenyl phosphate), monomeric aromatic phosphate ester compounds (e.g., triphenyl phosphate and tricresyl phosphate) and the like. In general, resorcinol-based phosphate ester flame retardants such as RDP have some more desirable properties over the bisphenol A-based phosphate ester flame retardants because of the presence of meta-phenylene linkages in the former.

Benzoylresorcinol (BR) has been used in the plastic and polymer industries to protect plastic and polymer materials against the harmful effects of the UV radiation from the sun. However, the use of benzoylresorcinol in flame retardants and their applications in plastics were not realized before. The use of benzoylresorcinol in the synthesis of phosphate ester type flame retardants may improve their UV resistance, thermal stability and possibly hydrolytic stability, in addition to flame retardant properties. In general, existing flame-retardant materials including the phosphorus flame retardants still cannot completely block the combustion of polymers. Therefore, there is a need for new benzoylresorcinol-based phosphate ester type flame retardants that have improved flame retardant properties and perhaps improved UV resistance.

SUMMARY OF THE INVENTION

Disclosed herein are new flame retardants that have desirable flame retarding and UV resistance properties.

In one aspect, the flame retardants comprise at least a phosphate ester compound having the formula:

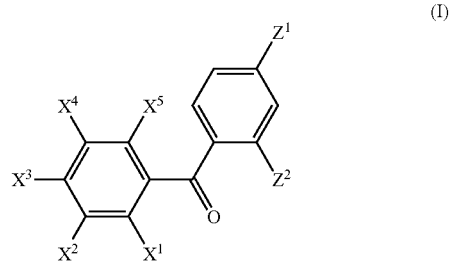

(I)

wherein each of $Z^1$ and $Z^2$ is independently a phosphate ester group;

each of $X^1$, $X^2$, $X^3$, $X^4$ and $X^5$ is independently hydrogen, halogen, nitro, cyano, acyl, alkyl, alkenyl, alkynyl, heteroalkyl, aryl, heteroaryl, cycloalkyl, or heterocycloalkyl, or $X^1$ and $X^2$, $X^2$ and $X^3$, $X^3$ and $X^4$, or $X^4$ and $X^5$ form a benzo group; and each of alkyl, alkenyl, alkynyl, heteroalkyl, aryl, heteroaryl, cycloalkyl, heterocycloalkyl or benzo is substituted or unsubstituted.

In some embodiments, the phosphate ester group has the formula:

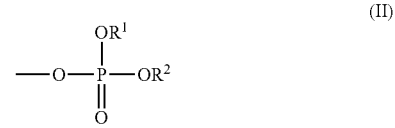

(II)

wherein each of $R^1$ and $R^2$ is independently alkyl, alkenyl, alkynyl, heteroalkyl, aryl, heteroaryl, cycloalkyl, or heterocycloalkyl, or a part of a heterocyclic group when $R^1$ and $R^2$ form the heterocyclic group together with the —O—P(=O)(—O—)—O— fragment; and each of alkyl, alkenyl, alkynyl, heteroalkyl, aryl, heteroaryl, cycloalkyl, heterocycloalkyl, and the heterocyclic group is substituted or unsubstituted.

Disclosed herein are also new processes of making flame retardants that have desirable flame retarding and UV resistance properties.

In one aspect, the process of preparing the flame retardant of Formula (I) where the phosphate ester group is represented by Formula (II) comprises the step of reacting a benzoylresorcinol compound having the formula:

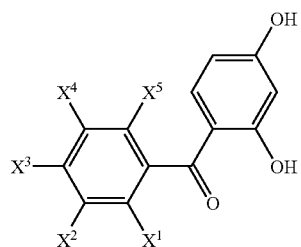

with a chlorophosphate having the formula:

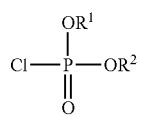

in the presence of a catalyst or an acid acceptor,
wherein each of $X^1$, $X^2$, $X^3$, $X^4$ and $X^5$ is independently hydrogen, halogen, nitro, cyano, acyl, alkyl, alkenyl, alkynyl, heteroalkyl, aryl, heteroaryl, cycloalkyl, or heterocycloalkyl, or $X^1$ and $X^2$, $X^2$ and $X^3$, $X^3$ and $X^4$, or $X^4$ and $X^5$ form a benzo group;

each of $R^1$ and $R^2$ is independently alkyl, alkenyl, alkynyl, heteroalkyl, aryl, heteroaryl, cycloalkyl, or heterocycloalkyl, or a part of a heterocyclic group when $R^1$ and $R^2$ form the heterocyclic group together with the —O—P(=O)(—O—)—O— fragment; and each of alkyl, alkenyl, alkynyl, heteroalkyl, aryl, heteroaryl, cycloalkyl, heterocycloalkyl, and the heterocyclic group is substituted or unsubstituted.

In another aspect, the process of preparing the flame retardants disclosed herein comprises the step of reacting a benzoylresorcinol compound having the formula:

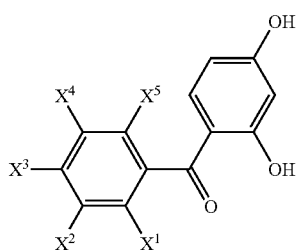

with phosphorus oxychloride in the presence of an acid acceptor,
wherein each of $X^1$, $X^2$, $X^3$, $X^4$ and $X^5$ is independently hydrogen, halogen, nitro, cyano, acyl, alkyl, alkenyl, alkynyl, heteroalkyl, aryl, heteroaryl, cycloalkyl, or heterocycloalkyl, or $X^1$ and $X^2$, $X^2$ and $X^3$, $X^3$ and $X^4$, or $X^4$ and $X^5$ form a benzo group; and each of alkyl, alkenyl, alkynyl, heteroalkyl, aryl, heteroaryl, cycloalkyl, and heterocycloalkyl is substituted or unsubstituted.

Disclosed herein are also new flame retardant compositions comprising a polymer and a flame retardant of Formula (I) and articles comprising the flame retardant compositions.

DESCRIPTION OF EMBODIMENTS OF THE INVENTION

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, RL and an upper limit, RU, is disclosed, any number falling within the range is specifically disclosed. In particular, the following numbers within the range are specifically disclosed: R=RL+k*(RU−RL), wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

Embodiments of the invention provide new benzoylresorcinol-based phosphate ester compounds which can function as flame retardants in compositions or articles comprising polymers such as polycarbonates (PC), poly(phenylene oxide) (PPO), polyesters (e.g., PET and PBT), polycarbonate and acrylonitrile-butadiene-styrene terpolymer (PC/ABS) blends, poly(phenylene oxide) and high-impact polystyrene (PPO/HIPS) blends, and other polymers. Such new benzoylresorcinol-based phosphate ester materials can be used as both flame retardants and UV stabilizers in plastics and other polymeric systems. These new flame retardants may possess enhanced thermal stability compared to resorcinol-based phosphate esters such as resorcinol bis(diphosphate) ester (RDP). Synthetic procedures to prepare benzoylresorcinol-based phosphate esters are also provided.

In some embodiments, this invention provides flame retardants having the formula:

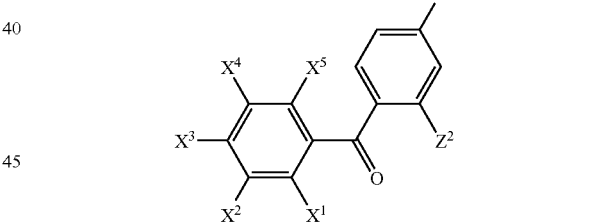

wherein each of $Z^1$ and $Z^2$ is independently a phosphate ester group; and
each of $X^1$, $X^2$, $X^3$, $X^4$ and $X^5$ is independently hydrogen, halogen, nitro, cyano, acyl, alkyl, alkenyl, alkynyl, heteroalkyl, aryl, heteroaryl, cycloalkyl, heterocycloalkyl, or a part of benzo group formed by $X^1$ and $X^2$, $X^2$ and $X^3$, $X^3$ and $X^4$, or $X^4$ and $X^5$ groups. Each of the alkyl, alkenyl, alkynyl, heteroalkyl, aryl, heteroaryl, cycloalkyl, heterocycloalkyl or benzo group is substituted or unsubstituted.

In some embodiments, each of $X^1$, $X^2$, $X^3$, $X^4$ and $X^5$ of Formula (I) is independently hydrogen. In other embodiments, each of $X^3$, $X^4$ and $X^5$ is independently hydrogen; and $X^1$ and $X^2$ together form a benzo group.

Each of $Z^1$ and $Z^2$ can be any known phosphate ester group. Further more, $Z^1$ and $Z^2$ can be the same or different in all embodiments including those disclosed herein. In some embodiments, the phosphate ester group has the formula:

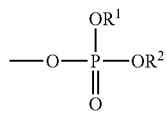
(II)

wherein each of $R^1$ and $R^2$ is independently alkyl, alkenyl, alkynyl, heteroalkyl, aryl, heteroaryl, cycloalkyl, or heterocycloalkyl. Each of alkyl, alkenyl, alkynyl, heteroalkyl, aryl, heteroaryl, cycloalkyl, and heterocycloalkyl may be substituted or unsubstituted. Non-limiting examples of the substituted alkyl group include aralkyls such as 4-(nitrophenyl) ethyl. Non-limiting examples of the substituted aryl group include halogenated aryls such as 2,4-dichlorophenyl and alkylated aryls or alkaryls such as 2-methylphenyl, 4-methylphenyl, and 3,5-dimethylphenyl.

In some embodiments, each of $R^1$ and $R^2$ of the phosphate ester group of Formula (II) is independently a part of a heterocyclic group when $R^1$ and $R^2$ form a heterocyclic group together with the —O—P(=O)(—O—)—O— fragment. The heterocyclic group may be substituted or unsubstituted. Non-limiting examples of such heterocyclic group include the following formulae:

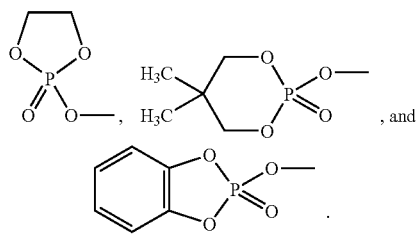

In some embodiments, each of $R^1$ and $R^2$ in Formula (II) is independently aryl. In other embodiments, each of $R^1$ and $R^2$ in Formula (II) is independently phenyl or naphthyl. In further embodiments, $R^1$ and $R^2$ in Formula (II) together form a heterocyclic group with the —O—P(=O)(—O—)—O— fragment in Formula (II). In particular embodiments, the phosphate ester group is selected from the group consisting of radicals having the following formulae:

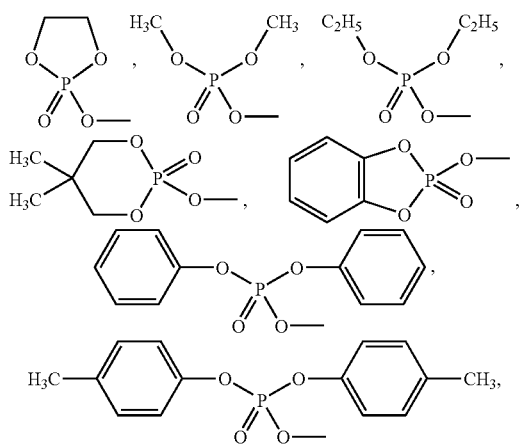

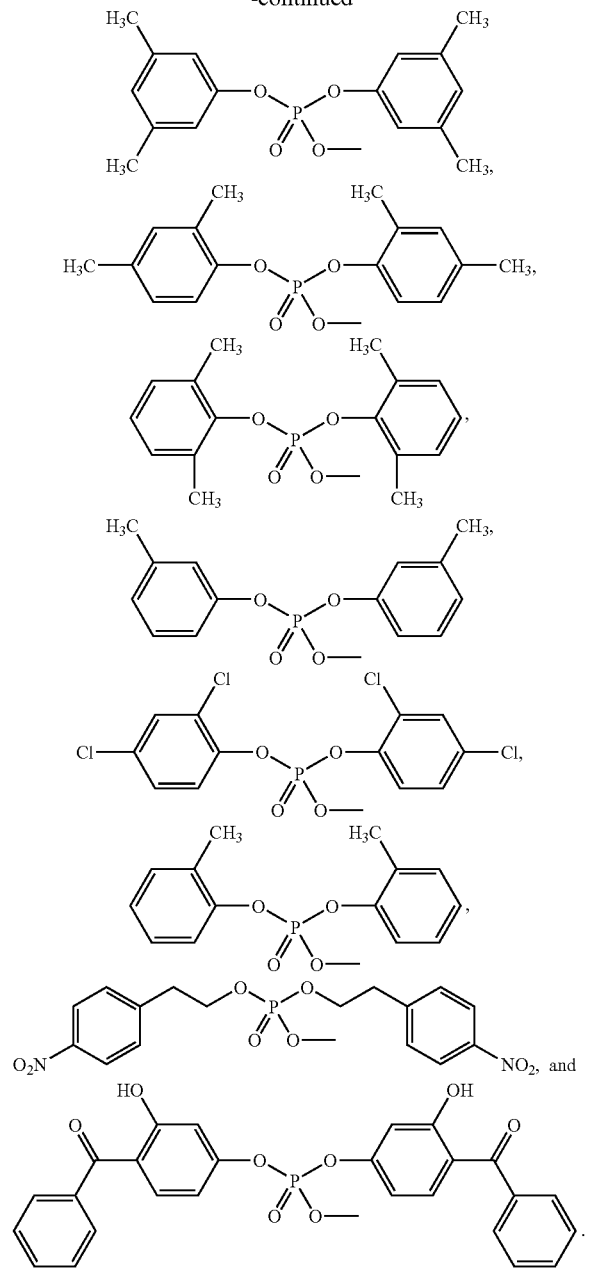

As used herein and unless otherwise indicated, the term "alkyl" or "alkyl group" means a univalent group having the general formula $C_nH_{2n+1}$ derived from removing a hydrogen atom from a saturated, unbranched or branched aliphatic hydrocarbon, where n is an integer, preferably between 1 and 20, more preferably between 1 and 8. Examples of alkyl groups include, but are not limited to, $(C_1\text{-}C_8)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl and octyl. Longer alkyl groups include nonyl and decyl groups. An alkyl group can be unsubstituted or substituted with one or more suitable substituents. Furthermore, the alkyl group can be branched or unbranched.

As used herein and unless otherwise indicated, the term "heteroalkyl" or "heteroalkyl group" means a univalent group derived from an alkyl group with at least one of the methylene group is replaced by a heteroatom or a hetero-group such as O, S, or NR where R is H or an organic group.

As used herein and unless otherwise indicated, the term "cycloalkyl" or "cycloalkyl group" means a univalent group derived from a cycloalkane by removal of a hydrogen atom from a non-aromatic, monocyclic or polycyclic ring comprising carbon and hydrogen atoms. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes and $(C_3-C_7)$cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two suitable substituents. Furthermore, the cycloalkyl group can be monocyclic or polycyclic.

As used herein and unless otherwise indicated, the term "heterocycloalkyl" or "heterocycloalkyl group" means a univalent group derived from a monocyclic or polycyclic heterocycloalkane by removal of a hydrogen atom from a ring carbon atom. Non-limiting examples of the heterocycloalkyl group include oxirane, thiirane, aziridine, oxetane, thietane, azetidine, pyrrolidine, tetrahydrothiophene, tetrahydrofuran, 2-pyrrolidinone, 2,5-pyrrolidinedione, dihydro-2(3H)-furanone, dihydro-2,5-furandione, dihydro-2(3H)-thiophenone, 3-aminodihydro-2(3H)-thiophenone, piperidine, 2-piperidinone, 2,6-piperidinedione, tetrahydro-2H-pyran, tetrahydro-2H-pyran-2-one, dihydro-2H-pyran-2,6(3H)-dione, and tetrahydro-4H-thiopyran-4-one. A heterocycloalkyl group can be unsubstituted or substituted with one or more suitable substituents. Furthermore, the heterocycloalkyl group can be monocyclic or polycyclic.

As used herein and unless otherwise indicated, the term "aryl" or "aryl group" means an organic radical derived from a monocyclic or polycyclic aromatic hydrocarbon by removing a hydrogen atom. Non-limiting examples of the aryl group include phenyl, naphthyl, benzyl, or tolanyl group, sexiphenylene, phenanthrenyl, anthracenyl, coronenyl, and tolanylphenyl. An aryl group can be unsubstituted or substituted with one or more suitable substituents. Furthermore, the aryl group can be monocyclic or polycyclic.

As used herein and unless otherwise indicated, the term "heteroaryl" or "heteroaryl group" means an organic radical derived from a monocyclic or polycyclic aromatic heterocycle by removing a hydrogen atom. Non-limiting examples of the heteroaryl group include furyl, thienyl, pyrrolyl, indolyl, indolizinyl, isoindolyl, pyrazolyl, imidazolyl, thiazolyl, thiadiazolyl, benzothiazolyl, 1,2,4-triazolyl, 1,2,3-triazolyl, indazolyl, benzotriazolyl, benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, and thianthrenyl. A heteroaryl group can be unsubstituted or substituted with one or more suitable substituents. Furthermore, the heteroaryl group can be monocyclic or polycyclic.

As used herein and unless otherwise indicated, the term "alkenyl" or "alkenyl group" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2-C_8)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butenyl)-pentenyl. An alkenyl group can be unsubstituted or substituted with one or two suitable substituents. Furthermore, the alkenyl group can be branched or unbranched.

As used herein and unless otherwise indicated, the term "alkynyl" or "alkynyl group" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_8)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents. Furthermore, the alkynyl group can be branched or unbranched.

As used herein and unless otherwise indicated, the term "heterocyclic" or "heterocyclic group" means any monocyclic or polycyclic (e.g., bicyclic, tricyclic, etc.) ring compound having at least a heteroatom (e.g., O, S, N, P, B, Si, etc.) in the ring. The heterocyclic group may be aromatic or non-aromatic.

As used herein and unless otherwise indicated, the term "substituted" as used to describe a compound or chemical moiety means that at least one hydrogen atom of that compound or chemical moiety is replaced with a second chemical moiety. The second chemical moiety can be any desired substituent that does not adversely affect the desired activity of the compound. Examples of substituents are those found in the exemplary compounds and embodiments disclosed herein, as well as halogen; alkyl; heteroalkyl; alkenyl; alkynyl; aryl, heteroaryl, hydroxyl; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); —O-lower alkyl; —O-aryl, aryl; aryl-lower alkyl; —$CO_2CH_3$; —$CONH_2$; —$OCH_2CONH_2$; —$NH_2$; —$SO_2NH_2$; —$OCHF_2$; —$CF_3$; —$OCF_3$; —NH(alkyl); —N(alkyl)$_2$; —NH(aryl); —N(alkyl)(aryl); —N(aryl)$_2$; —CHO; —CO(alkyl); —CO(aryl); —$CO_2$(alkyl); and —$CO_2$(aryl); and such moieties can also be optionally substituted by a fused-ring structure or bridge, for example —$OCH_2O$—. These substituents can optionally be further substituted with a substituent selected from such groups. All chemical groups disclosed herein can be substituted, unless it is specified otherwise.

Flame retardant compositions having improved flammability characteristics can be formulated by adding at least a flame retardant of Formula (I) to at least a polymer. Non-limiting examples of polymers include polycarbonates (PC), poly(phenylene oxide) (PPO), polyesters (e.g., PET and PBT), acrylonitrile-butadiene-styrene terpolymer (ABS), high-impact polystyrene (HIPS), polyarylates and combinations or blends thereof such as the polycarbonate and acrylonitrile-butadiene-styrene terpolymer (PC/ABS) blend and the poly(phenylene oxide) and high-impact polystyrene (PPO/HIPS) blend. In some embodiments, the flame retardant compositions further comprise at least one flame retardant known in the art such as phosphate esters (e.g., RDP), alumina trihydrate, magnesium hydroxide, halogenated compounds, antimony oxide, melamine derivatives, and boric acid and other boron compounds. In other embodiments, the flame retardant compositions are substantially free of a second flame retardant known in the art, which can be selected from the group consisting of phosphate esters, alumina trihydrate, magnesium hydroxide, halogenated compounds, antimony oxide, melamine derivatives, boric acid and other boron compounds, and combinations thereof. As used herein and unless otherwise indicated, a composition that is "substantially free" of a compound or an additive means that the composition contains less than about 20% by weight, more preferably less than about 10% by weight, even more preferably less than about 5% by weight, and most preferably less than about 3% by weight of the compound or the additive.

Optionally, the flame retardant compositions can further comprise at least one additive such as extenders, fibers, fillers, coupling agents, cross-linking agents, plasticizers, impact modifiers, compatibilizers, anti-blocking agents, anti-fogging agents, anti-aging agents, antioxidants, UV stabilizers, antiozonants, acid scavengers, processing aids, surfactants, lubricants, plasticizing agents, parting agents and abherents, nucleating agents, anti-static agents, slip agents, chemical blowing agents, fluorescent whitening agents, flow agents, deodorants, release agents, colorants such as dye and pigments, and anti-microbials such as bactericides. Some of the above-mentioned additives are described in Zweifel, et al., "*Plastics Additives Handbook*," Hanser Gardner Publications, Cincinnati, Ohio, 5th edition (2001); John Murphy, "*Additives for Plastics Handbook*," Elsevier Science Pub. Co., New York, N.Y., 2nd edition (2001), both of which are incorporated herein by reference in their entirety. In some embodiments, the flame retardant compositions are substantially free of an additive. In a particular embodiment, the flame retardant compositions are substantially free of a UV stabilizer.

The flame retardant compositions can be used to prepare articles by known polymer processes such as extrusion, injection molding and molding such as rotational molding. In general, extrusion is a process by which a polymer is propelled continuously along a screw through regions of high temperature and pressure where it is melted and compacted, and finally forced through a die. The extrusion of polymers is described in C. Rauwendaal, "*Polymer Extrusion*", Hanser Publishers, New York, N.Y. (1986); and M. J. Stevens, "*Extruder Principals and Operation*," Elsevier Applied Science Publishers, New York, N.Y. (1985), both of which are incorporated herein by reference in their entirety.

Injection molding is also widely used for manufacturing a variety of plastic parts for various applications. In general, injection molding is a process by which a polymer is melted and injected at high pressure into a mold, which is the inverse of the desired shape, to form parts of the desired shape and size. The mold can be made from metal, such as steel and aluminum. The injection molding of polymers is described in Beaumont et al., "*Successful Injection Molding: Process,*

*Design, and Simulation*," Hanser Gardner Publications, Cincinnati, Ohio (2002), which is incorporated herein by reference in its entirety.

Molding is generally a process by which a polymer is melted and led into a mold, which is the inverse of the desired shape, to form parts of the desired shape and size. Molding can be pressureless or pressure-assisted. The molding of polymers is described in Hans-Georg Elias "*An Introduction to Plastics*," Wiley-VCH, Weinhei, Germany, pp. 161-165 (2003), which is incorporated herein by reference. Rotational molding is a process generally used for producing hollow plastic products. By using additional post-molding operations, complex components can be produced as effectively as other molding and extrusion techniques.

Rotational molding differs from other processing methods in that the heating, melting, shaping, and cooling stages all occur after the polymer is placed in the mold, therefore no external pressure is applied during forming. The rotational molding of polymers is described in Glenn Beall, "*Rotational Molding: Design, Materials & Processing*," Hanser Gardner Publications, Cincinnati, Ohio (1998), which is incorporated herein by reference in its entirety.

In general, any article that comprises a polymer can be obtained with a flame retardant composition which contains the polymer and at least a flame retardant of Formula (I). Non-limiting examples of useful articles include plastic products, textiles, wood and paper products, adhesives and sealants, and rubber products, aerospace parts, automotive parts, wires, cables, construction materials, materials for interiors and furnishings, appliances, electronic components, computers, and business machines. In some embodiments, the articles are prepared by extrusion of the flame retardant composition. In other embodiments, the articles are prepared by injection molding of the flame retardant composition. In further embodiments, the articles are prepared by molding of the flame retardant composition. In additional embodiments, the articles are prepared by rotational molding of the flame retardant composition.

In some embodiments, the flame retardants of Formula (I) can be obtained by the process of reacting a benzoylresorcinol compound having the formula:

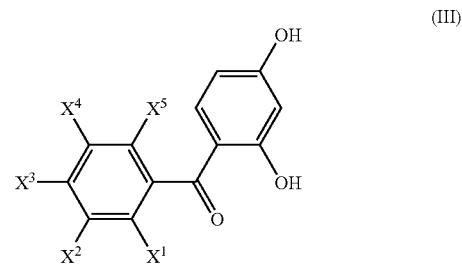

(III)

with a chlorophosphate having the formula:

(IV)

in the presence of a catalyst or an acid acceptor, wherein $X^1$, $X^2$, $X^3$, $X^4$, $X^5$, $R^1$ and $R^2$ are as defined above.

As used herein and unless otherwise indicated, the term "reacting" or the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein and unless otherwise indicated, a reaction that is "substantially complete" or is driven to "substantial completion" means that the reaction contains more than about 80% by percent yield, more preferably more than about 90% by percent yield, even more preferably more than about 95% by percent yield, and most preferably more than about 97% by percent yield of the desired product.

The phosphorylation of Formula (III) with Formula (IV) can be promoted by either a catalyst such as magnesium chloride (as in Scheme A) or an acid acceptor such organic bases (as in Scheme B). The phosphorylation can occur in a solvent, preferably an inert organic solvent which does not react with the chloro group of the compound of formula (IV). Non-limiting examples of suitable inert organic solvents include aromatic hydrocarbons (e.g., toluene, benzene, and xylene), methylene chloride, chloroform, acetonitrile, ethers, ketones, dimethylformamide, trichloroethane, tetrahydrofuran, tetrachloroethylene, chlorobenzene and combinations thereof. In some embodiments, the solvent is toluene or methylene chloride.

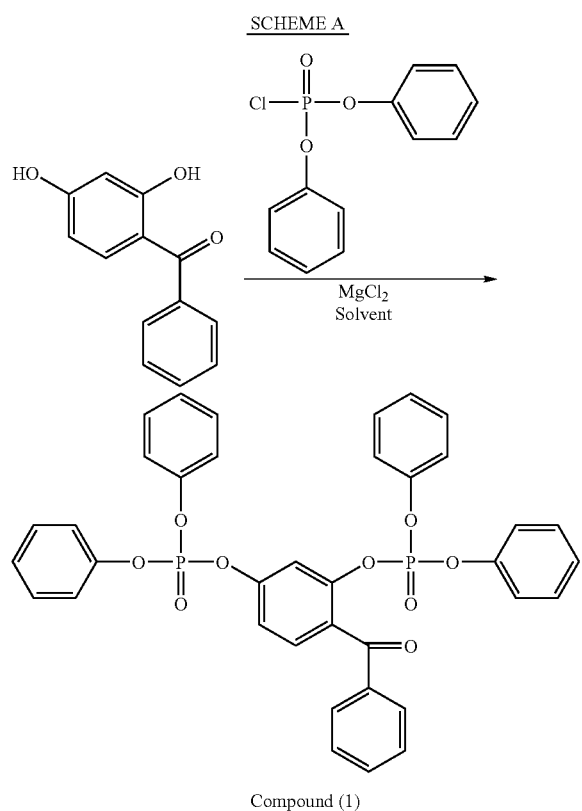

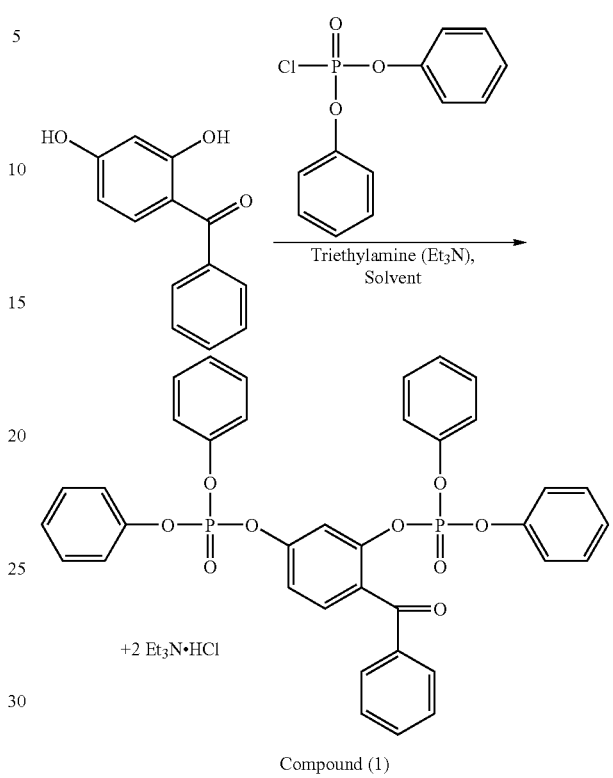

The acid acceptor can be an organic base. Non-limiting examples of suitable organic bases include amines (e.g., trimethylamine, triethyl amine, N,N-diisopropylethylamine, triphenylamine, 1,8-diazabicyclo[5.4.8]undec-7-ene), 1-alkylpiperidines such as 1-ethylpiperidine, 1-alkylpyrrolidines such as 1-methylpyrrolidine, pyridine, and combinations thereof. Other suitable amines include, but not limited to, trialkylamines such as tributylamine, trioctylamine, trinonylamine, tridecylamine, triundecylamine, tridodecylamine, tri(tridecyl)amine, tripentadecylamine, trihexadecylamine, triheptadecylamine, trioctadecylamine, trinonadecylamine, trieicosylamine, tri(tetrachlorododecyl)amine, trihexachloroheptadecylamine, lower alkyl substituted derivatives of pyridine (such as 2,6-lutidine and 2,4,6-collidine), 2,2,6,6-N-pentamethylpiperidine, N,N-dimethylaniline, and diisopropyl-N-ethylamine or combinations thereof. In some embodiments, the acid acceptor is triethylamine.

Any phosphorylation catalyst known by a person of ordinary skill in the art can be used for the reaction between Formula (III) and $POCl_3$. Non-limiting examples of phosphorylation catalysts include magnesium chloride, aluminum trichloride, titanium tetrachloride, and zinc dichloride. In some embodiments, the solvent for the magnesium chloride-catalyzed phosphorylation is toluene and the reaction temperature is greater than about 35° C., preferably greater than about 55° C., more preferably greater than about 75° C., and most preferably greater than about 100° C. The reaction product can be purified by washing the reaction mixture after completion with water or a basic aqueous solution such as sodium hydroxide solution, sodium carbonate solution, sodium bicarbonate solution, or potassium hydroxide solution. The amount of the catalyst can be in the range from 0.1 wt % to 10 wt % based on the total weight of the reactants. The reaction temperature can be greater than 25° C., greater than 50° C., greater than 75° C., greater than 100° C., greater than 120° C., greater than 140° C., or greater than 150° C.

In other embodiments, such as that depicted in Scheme B, the acid acceptor is triethylamine. In further embodiments, the solvent for the triethylamine-promoted phosphorylation is methylene chloride and the reaction temperature is less than about 50° C., preferably less than about 35° C., and more preferably between about 20° C. and about 25° C. The amount of the acid acceptor can be in the range from 2.0 to 3.0 moles per mole of the benzoylresorcinol derivative of the Formula (III).

The mole ratio of the benzoylresorcinol compound of Formula (III) to the chlorophosphate of Formula (IV) can be between about 1:1.5 and about 1:2.5. In a particular embodiment, the ratio of the benzoylresorcinol compound of Formula (III) to the chlorophosphate of Formula (IV) is about 1:2. In some embodiments, where an excess of either the benzoylresorcinol compound of Formula (III) or the chlorophosphate of Formula (IV) is used, the excess unreacted reactant can be extracted or separated out with a combination of water and/or an aqueous basic solution and/or acidic solution.

The chlorophosphate of Formula (IV) can be any chlorophosphate that can react with the aromatic hydroxyl groups of Formula (III). Non-limiting examples of suitable chlorophosphates of Formula (IV) include 2-chloro-2-oxo-1,3,2-dioxaphospholane, dimethyl chlorophosphate, diethyl chlorophosphate, 2-chloro-5,5-dimethyl-1,3,2-dioxaphophorinane-2-oxide, o-phenylene phosphorochloridate, diphenyl chlorophosphate, bis(2-methylphenyl) chlorophosphate, bis(4-methylphenyl) chlorophosphate, bis(3,5-dimethylphenyl) chlorophosphate, bis(2,6-dimethylphenyl) chlorophosphate, bis(2,4-dichlorophenyl) chlorophosphate, and bis[2-(4-nitrophenyl)ethyl] chlorophosphate, all of which are available from a commercial supplier such as Aldrich Chemicals, Milwaukee, Wis. In a particular embodiment, the chlorophosphate of Formula (IV) is diphenyl chlorophosphate.

The benzoylresorcinol compound of Formula (III) can be 2,4-dihydroxybenzophenone or any one of its derivatives that can react with the chlorophosphate of Formula (IV). In some embodiments, each of $X^1$, $X^2$, $X^3$, $X^4$ and $X^5$ is independently selected from the group consisting of halogen, nitro, cyano, acyl, alkyl, aralkyl, alkenyl, alkynyl, heteroalkyl, aryl, heteroaryl, cycloalkyl, and heterocycloalkyl. In other embodiments, none of $X^1$, $X^2$, $X^3$, $X^4$ and $X^5$ of Formula (III) is a functional group (such as hydroxyl, amine, thiol, and carboxyl) that can react with the chloro group of the chlorophosphate of Formula (IV). In further embodiments, any pair of adjacent X groups (i.e., $X^1$ and $X^2$, $X^2$ and $X^3$, $X^3$ and $X^4$, or $X^4$ and $X^5$ groups) in Formula (III) together can form a benzo ring substituent. In some embodiments, each of $X^1$, $X^2$, $X^3$, $X^4$ and $X^5$ is independently hydrogen. In other embodiments, each of $X^3$, $X^4$ and $X^5$ is independently hydrogen; and $X^1$ and $X^2$ together form a benzo group. Non-limiting examples of suitable benzoylresorcinol compounds of Formula (III) include 2,4-dihydroxybenzophenone and 2,4-dihydroxyphenyl-1-naphthyl ketone, both of which can be obtained from a commercial supplier such as Aldrich Chemicals.

In other embodiments, flame retardants can be obtained by reacting a benzoylresorcinol compound having the formula:

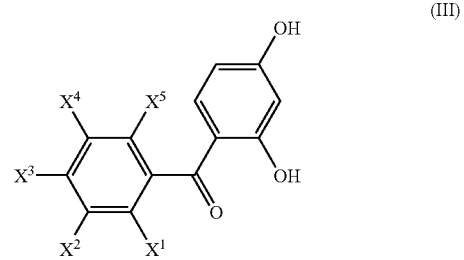

with phosphorus oxychloride ($POCl_3$) in the presence of a catalyst or an acid acceptor, wherein each of $X^1$, $X^2$, $X^3$, $X^4$ and $X^5$ is independently hydrogen, halogen, nitro, cyano, acyl, alkyl, alkenyl, alkynyl, heteroalkyl, aryl, heteroaryl, cycloalkyl, heterocycloalkyl, or a part of benzo group formed by $X^1$ and $X^2$, $X^2$ and $X^3$, $X^3$ and $X^4$, or $X^4$ and $X^5$ groups.

The reaction between benzoylresorcinol compound of Formula (III) and $POCl_3$ can occur in a solvent such as aromatic hydrocarbons (e.g., toluene, benzene, and xylene), methylene chloride, chloroform, acetonitrile, ethers, ketones, dimethylformamide, trichloroethane, tetrahydrofuran, tetrachloroethylene, chlorobenzene and combinations thereof.

Any compound that can neutralize hydrogen chloride can be used as an acid acceptor for this invention. In some embodiments, the acid acceptor is an organic base. Non-limiting examples of suitable organic bases include amines (e.g., trimethylamine, triethylamine, N,N-diisopropylethylamine, triphenylamine, 1,8-diazabicyclo[5.4.0]undec-7-ene), 1-alkylpiperidines such as 1-ethylpiperidine, 1-alkylpyrrolidines such as 1-methylpyrrolidine, pyridine, and combinations thereof. Other suitable amines include, but are not limited to, trialkylamines such as tributylamine, trioctylamine, trinonylamine, tridecylamine, triundecylamine, tridodecylamine, tri(tridecyl)amine, tripentadecylamine, trihexadecylamine, triheptadecylamine, trioctadecylamine, trinonadeclyamine, trieicosylamine, tri(tetrachlorododecyl)amine, trihexachloroheptadecylamine, lower alkyl substituted derivatives of pyridine (such as 2,6-lutidine and 2,4,6-collidine), 2,2,6,6-N-pentamethylpiperidine, N,N-dimethylaniline, and diisopropyl-N-ethylamine or combinations thereof. In some embodiments, the acid acceptor is triethylamine. In one embodiment, the solvent is methylene chloride. In another embodiment, the solvent is toluene. In further embodiments, the reaction temperature is less than 50° C., preferably less than 35° C., and more preferably between about 20° C. and about 25° C.

Any phosphorylation catalyst known by a person of ordinary skill in the art can be used for the reaction between Formula (III) and $POCl_3$. Non-limiting examples of phosphorylation catalysts include magnesium chloride, aluminum trichloride, titanium tetrachloride, and zinc dichloride. The reaction product can be purified by washing the reaction mixture after completion with water or a basic aqueous solution such as sodium hydroxide solution, sodium carbonate solution, sodium bicarbonate solution, or potassium hydroxide solution. The amount of the catalyst can be in the range from 0.1 wt % to 10 wt % based on the total weight of the reactants. The reaction temperature can be greater than 25° C., greater than 50° C., greater than 75° C., greater than 100° C., greater than 120° C., greater than 140° C., or greater than 150° C.

The benzoylresorcinol compound of Formula (III) can have at least one substituent selected from the group consisting of halogen, nitro, cyano, acyl, alkyl, alkenyl, alkynyl, heteroalkyl, aryl, heteroaryl, cycloalkyl, and heterocycloalkyl. It is preferred that none of $X^1$, $X^2$, $X^3$, $X^4$ and $X^5$ of Formula (III) is a functional group (such as hydroxyl, amine, thiol, and carboxyl) that can react with the chlorophosphate of Formula (IV). In some embodiments, each of $X^1$, $X^2$, $X^3$, $X^4$ and $X^5$ is independently hydrogen, i.e., the benzoylresorcinol compound of Formula (III) is 2,4-dihydroxybenzophenone. The reaction between 2,4-dihydroxybenzophenone and $POCl_3$ and some of the reaction products are depicted in Scheme C below.

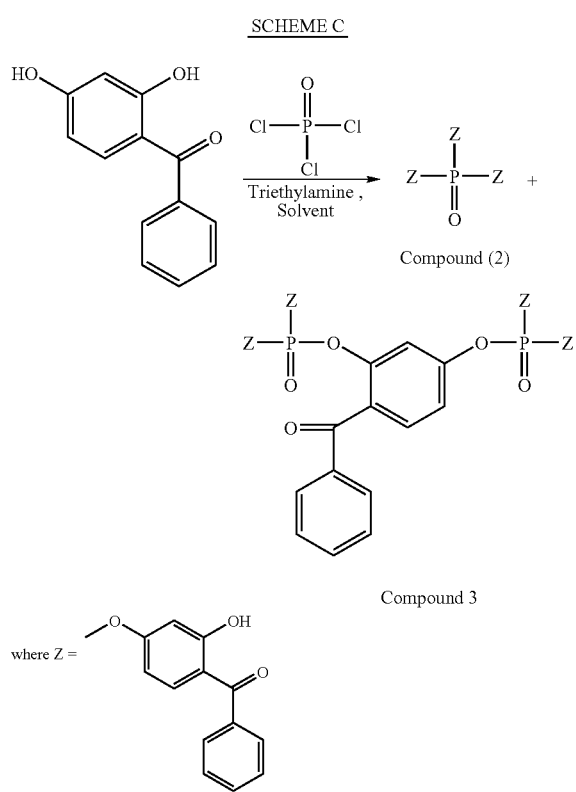

SCHEME C

Compound (2)

Compound 3 where Z =

In general, the reaction between 2,4-dihydroxybenzophenone and $POCl_3$ can produce a mixture of compounds including, inter alia, Compound (2) and Compound (3) and perhaps unreacted starting material(s), the ratios of which depend on the ratio of the two starting materials and the reaction conditions.

The mole ratio of the benzoylresorcinol compound of Formula (III) to $POCl_3$ can be between about 3.5:1 and 1.5:1, preferably between about 3.1:1 and 2:1. In some embodiments where the benzoylresorcinol compound of Formula (III) is 2,4-dihydroxybenzophenone, the mole ratio of the benzoylresorcinol compound of Formula (III) to $POCl_3$ is between about 2.1:1 and about 3.1:1. In other embodiments where an excess of the benzoylresorcinol compound of Formula (III) or $POCl_3$ is used, the excess unreacted reactant can be extracted or separated out with an aqueous basic solution or water.

Based on the disclosure herein, a person of ordinary skill in the art can recognize that other benzoyl-based phosphate esters, in addition to those represented by Formula (I), can be obtained from other benzoyl compounds having at least two aromatic hydroxy groups such as 3,4-dihydroxybenzophenone, 2,6-dihydroxybenzophenone or 3,5-dihydroxybenzophenone.

The following examples are presented to exemplify embodiments of the invention. All numerical values are approximate. When numerical ranges are given, it should be understood that embodiments outside the stated ranges may still fall within the scope of the invention. Specific details described in each example should not be construed as necessary features of the invention.

EXAMPLES

Synthesis of Benzoylresorcinol-Based Phosphate Ester Compounds

Some benzoylresorcinol-based phosphate ester flame retardants of Formula (I) can be synthesized using the benzoylresorcinol compound of Formula (III) as a reactant. In some embodiments, the benzoylresorcinol compound of Formula (III) is 2,4-dihydroxybenzophenone which can react with diphenyl chlorophosphate (DPCP) to produce Compound (1), a benzoylresorcinol-based bis(diphenyl phosphate). The reaction can be completed via two different routes: (1) by a high temperature reaction, e.g., Scheme A using magnesium chloride ($MgCl_2$) as a catalyst; and (2) by a low temperature reaction, e.g., Scheme B using triethylamine as a catalyst.

In some embodiments, the reaction of the benzoylresorcinol of Formula (III) with diphenyl chlorophosphate in the presence of $MgCl_2$ catalyst at an elevated temperature can produce Compound (1) as shown in Scheme A above. The synthesis procedures developed to prepare Compound (1) according to Scheme A are given below.

Example 1

Benzoylresorcinol (214.2 grams, 1.0 mole), diphenyl chlorophosphate (97.6%; 550.5 grams, 2.0 moles), and toluene (500 mL) were charged in a 3 L round-bottom flask with a mechanical stirrer, a thermometer, a nitrogen port, a reflux condenser, a caustic trap, and a heating mantle. The contents were stirred under a $N_2$ sweep for 10 minutes. After $MgCl_2$ (5.4 grams) was added to the reaction mixture, the temperature was increased to 105° C. The temperature was maintained at 105° C. until the evolution of hydrogen chloride (HCl) gas stopped (approximately 13 hours). After toluene (720 grams) was added to the reaction mixture, the reaction mixture was washed 3 times with water (200 grams each). Next, toluene was removed by distillation under a reduced pressure. The product (676.7 grams) was an orange-amber viscous liquid. A C-13 NMR analysis indicated 100 mole % of aromatic C—O—P carbons and no detectable C—OH carbons, which is consistent with the desired product. The product was found to contain 9.3 wt % phosphorus and to have a viscosity of 800 centipoise at 50° C. and a density of 1.30 at 25° C.

Example 2

Benzoylresorcinol (214.2 grams, 1.0 mole), diphenyl chlorophosphate (97.6%; 550.5 grams, 2.0 moles), and toluene (900 mL) were charged in a 2 L round-bottom flask with a mechanical stirrer, a thermometer, a nitrogen port, a reflux condenser, a caustic trap, and a heating mantle. The contents were stirred under a $N_2$ sweep for 10 minutes. After $MgCl_2$ (5.4 grams) was added to the reaction mixture, the temperature was increased to 105° C. The temperature was maintained at 105° C. until the evolution of hydrogen chloride (HCl) gas stopped (approx. 21 hrs). After toluene (600 grams) was added to the reaction mixture, the reaction mixture was washed with 2% sodium hydroxide (NaOH) solution (200 grams), 1% NaOH solution (200 grams), and 2 times with water (200 grams each). Next, toluene was removed by distillation under reduced pressure. The product (641.7 grams) was an orange-amber viscous liquid with a number average molecular weight of 666±16. A C-13 NMR analysis indicated 100 mole % of aromatic C—O—P carbons and no detectable C—OH carbons, which is consistent with the desired product.

In some embodiments, the benzoylresorcinol-based phosphate ester compound can also be synthesized using a low temperature solution process according to Scheme B. The synthesis procedure developed to prepare Compound (1) according to Scheme B is given below.

Example 3

Benzoylresorcinol (6.4 grams, 0.03 mole), diphenyl chlorophosphate (97.6%; 16.5 grams, 0.06 mole), and methylene chloride (80 mL) were charged in a 500 mL round-bottom flask with a mechanical stirrer, a thermometer, an addition funnel, a reflux condenser with a calcium chloride ($CaCl_2$) tube, and a heating mantle. The contents were stirred at 20-25° C. After a solution of triethylamine (6.1 grams, 0.06 mole) dissolved in methylene chloride (40 mL) was added dropwise to the flask for 1 hour at 20-25° C., the temperature was maintained for an additional 4 hours. After the mixture was washed with water six times at 35° C., the methylene chloride was removed at 95° C. under vacuum (28 in. Hg) using a rotary evaporator. The product (20.2 grams) was a yellow viscous liquid. FT-IR analysis confirmed the following structures were present in the product: —OH (very weak), aryl ring, aryl ketone carbonyl (C=O), aryl-O, P=O, P—O—C, and monosubstituted benzene ring. A C-13 NMR analysis indicated 98 mole % of aromatic C—O—P carbons and 2 mole % of aromatic C—OH carbons.

Thermal Stability Data

The thermal stabilities of the benzoylresorcinol-based phosphate ester compound of Example 1 and FYROLFLEX® RDP, a control, were determined by thermogravimetric analysis (TGA) under air at a scan rate of 110° C./minute in the temperature range between 25° C. and 700° C. FYROLFLEX® RDP is a resorcinol diphenylphosphate ester flame retardant available from Akzo Nobel Chemical Inc., Dobbs Ferry, N.Y. The TGA analysis results of Example 1 and FYROLFLEX® RDP are presented in Table 1.

TABLE 1

| Weight Loss by TGA: | Temperature (° C.) at Given Weight Loss | | | | |
| --- | --- | --- | --- | --- | --- |
| | 1% | 5% | 10% | 25% | 50% |
| Control (FYROLFLEX ® RDP)* | 248 | 309 | 346 | 383 | 410 |
| Example 1 (A Benzoylresorcinol-based Phosphate Ester) | 266 | 319 | 340 | 364 | 430 |

Note:
*FYROLFLEX ® RDP is a resorcinol diphenylphosphate ester flame retardant available from Akzo Nobel Company.

The data shown in Table 1 suggest that Example 1, a benzoylresorcinol-based phosphate ester, exhibits a higher thermal stability than FYROLFLEX® RDP, a resorcinol-based phosphate ester. This enhanced thermal stability might be associated with the presence of benzoyl group in the structure of Example 1.

Polymer Processing and Testing

Examples 4(a) and (b)

The benzoylresorcinol-based flame retardant of Example 1 was added into a polycarbonate and acrylonitrile-butadiene-styrene terpolymer (PC/ABS) blend in a Coperion ZSK-30 twin-screw extruder (obtained from Coperion Corporation, Ramsey, N.J.) at two different loadings to provide Examples 4(a) and 4(b) respectively. The loading of each example was indicated by its phosphorus content in Table 2. The PC/ABS blend used was a specially formulated blend that lacks any flame retardant but contains the same PC/ABS terpolymer in commercially available BAYBLEND® FR2010. The skilled artisan will recognize that BAYBLEND® FR2010 (Bayer Material Science, Pittsburgh, Pa.) has a flame retardant incorporated therein. The twin-screw extruder was operated at approximately 55-65 g/minute flow rate and the barrel temperature profile was (in direction from feed to nozzle): 190, 240, 240, 245, 250, 257° C. The flame retardant was added using a liquid addition system consisting of a heated reservoir and tubing, Zenith gear pump, and liquid addition nozzle. The liquid addition system was held at 62° C. The flame retardant was added to the extruder at 120 psi (827 kPa) through a liquid injection nozzle. The flame retardant-containing pellets were dried and molded into test specimens using an Arburg Allrounder injection molder, with the following temperature profile from feed to nozzle of: 243, 253, 258, 265° C. The mold temperature was 190° F. (87.8° C.). Specimens were conditioned for more than 40 hours at 23° C. and 50% humidity. The phosphorus content, heat deflection temperature, melt flow index, notched IZOD impact strength, tensile strength and modulus, flexural modulus, and flammability property of the sample were evaluated. The results, along with those of comparative examples (Controls 1 and 2), are shown in Table 2.

Comparative Example 1 (Control 1)

Test specimens of BAYBLEND® FR2010 were injection molded as described in Examples 4(a) and 4(b) above. The phosphorus content, heat deflection temperature, melt flow index, notched IZOD impact strength, tensile strength and modulus, flexural modulus, and flammability property of Control 1 were evaluated. The results are listed in Table 2.

Comparative Example 2 (Control 2)

The commercial flame retardant FYROLFLEX® RDP (Akzo Nobel Functional Chemicals LLC), a resorcinol bis (diphenyl phosphate), was added into the specially formulated PC/ABS blend of Example 4 in the twin-screw extruder as was performed in Examples 4(a) and 4(b) above. Test specimens were then injection molded. The phosphorus contents, heat deflection or distortion temperatures, melt flow indexes, notched IZOD impact strength, tensile strength and moduli, flexural moduli, and flammability properties Controls 1 and 2 and Examples 4(a) and 4(b) were evaluated. The results are listed in Table 2.

The phosphorus content of each of Controls 1 and 2 and Examples 4(a) and 4(b) was measured by the following spectrophotometric technique. A sample was decomposed by treatment with sulfuric acid and nitric acids, and then boiled in a dilute acid to convert phosphate groups in the sample to ortho-phosphate. The ortho-phosphate was complexed with ammonium molybdate and ammonium vanadate in an acid solution. The amount of ortho-phosphate and thus the phosphorus content was measured spectrophotometrically by a Beckman UV/Visible spectrophotometer (model DU, from Beckman Coulter, Inc., Fullerton, Calif.) at a wavelength of 470 nm.

The heat deflection temperature at 264 psi fiber stress of each sample was measured by ASTM D648. The melt flow index of each sample was measured by ASTM D1238. The notched IZOD impact strength of each sample was measured by ASTM D256. The tensile strength and modulus of each sample were measured by ASTM D638. The flexural modulus of each sample was measured by ASTM D790. The flammability property of each sample was measured by Underwriters Laboratories UL-94 vertical burn test. All of the above standard tests are incorporated herein by reference.

TABLE 2

|  | Control 1 | Control 2 | Example 4(a) | Example 4(b) |
|---|---|---|---|---|
| Phosphorus Content in PC/ABS (Weight %) | 0.99 | 1.01 | 0.99 | 0.80 |
| Physical Properties | | | | |
| Melt Flow Index (g/10 Min) | 28.6 | 26.1 | 27.7 | 23.3 |
| Heat Deflection Temp. (° C.) | 90.5 | 90.0 | 90.5 | 94.4 |
| Notched Izod (ft-lb/in) | 11.2 | 9.8 | 9.1 | 10.0 |
| Tensile Properties | | | | |
| Strength (MPa) | 58.5 | 57.7 | 59.2 | 59.5 |
| Modulus (GPa) | 2.77 | NA | 2.48 | 2.48 |
| Flexural Property | | | | |
| Modulus (GPa) | 2.83 | 2.78 | 2.58 | 2.66 |
| Flammability Testing - UL-94 Vertical Burn Test | | | | |
| Flammability Rating (1/16") | V-0 | V-0 | V-0 | V-0 |
| Total After Flame Time (sec., set of 5 samples) | 16.9 | 9.4 | 4.9 | 32.6 |

Note:
*Upon burning in the UL-94 test, the specimens dripped and ignited the cotton.

Examples 5(a) and (b)

The flame retardant described in Example 2 was added into the specially formulated PC/ABS blend of Example 4 in a Coperion ZSK-30 twin-screw extruder at two different loadings to provide Examples 5(a) and 5(b) respectively. The loading of each example was indicated by its phosphorus content in Table 3. The twin-screw extruder was operated at approximately 55-65 g/minute flow rate and the barrel temperature profile was (in direction from feed to nozzle): 190, 240, 240, 245, 250, 257° C. The flame retardant was added using a liquid addition system consisting of a heated reservoir and tubing, Zenith gear pump, and liquid addition nozzle. The liquid addition system was held at 62° C. The flame retardant was added to the extruder at 120 psi (827 kPa) through a liquid injection nozzle. The flame retardant-containing pellets were dried and molded into test specimens using an Arburg Allrounder injection molder, with the following temperature profile from feed to nozzle: 243, 253, 258, 265° C. The mold temperature was 190° F. Specimens were conditioned for greater than 40 hours at 23° C. and 50% humidity. The phosphorus content, heat deflection temperature, melt flow index, notched IZOD impact strength, tensile strength and modulus, flexural modulus, and flammability property of the samples were evaluated. The results, along with those of comparative examples (Controls 1 and 2), are shown in Table 3.

TABLE 3

|  | Control 1 | Control 2 | Example 5(a) | Example 5(b) |
|---|---|---|---|---|
| Phosphorus Content in PC/ABS (Weight %) | 0.99 | 1.01 | 0.87 | 1.17 |
| Physical Properties | | | | |
| Melt Flow Index (g/10 Min) | 28.6 | 26.1 | 19.3 | 26.5 |
| Heat Distortion Temperature (° C.) | 90.5 | 90.0 | 96.3 | 90.0 |
| Notched Izod (ft-lb/in) | 11.2 | 9.8 | 10.2 | 4.8 |
| Tensile Properties | | | | |
| Strength (MPa) | 58.5 | 57.7 | 60.0 | 60.8 |
| Modulus (GPa) | 2.77 | NA | 2.72 | 2.79 |
| Flexural Property | | | | |
| Modulus (GPa) | 2.83 | 2.78 | 2.65 | 2.75 |
| Flammability Testing - UL-94 Vertical Burn Test | | | | |
| Flammability Rating (1/16") | V-0 | V-0 | V-0 | V-0 |
| Total After Flame Time (sec., set of 5 samples) | 16.9 | 9.4 | 12.0 | 2.2 |

In some embodiments, the benzoylresorcinol-based phosphate ester compound can also be synthesized using the process according to Scheme C. The synthesis procedures according to Scheme C are given below.

Example 6

Phosphorus oxychloride (7.8 grams, 0.051 mole) and toluene (200 mL) were charged in a 500 mL round-bottom flask with a mechanical stirrer, a thermometer, an addition funnel, and a reflux condenser with a $CaCl_2$ tube. After the contents were stirred and cooled to 0-5° C., benzoylresorcinol (25.7 grams, 0.12 mole) was added. A solution of triethylamine (16.3 grams, 0.16 mole) dissolved in toluene (50 mL) was added dropwise for 1 hour at 0-5° C. The temperature was raised to 20-25° C. and held for 3 hours. The precipitate (triethylamine-HCl salts) was filtered out and the toluene was removed with a rotary vacuum evaporator. The resultant material (28.9 grams) was re-dissolved in methylene chloride (150 ml) and washed 3 times with water at 35° C. The methylene chloride was removed with a rotary vacuum evaporator. The final product was a yellow powder. A C-13 and proton NMR analysis revealed the following structures: 75 mole % of "monophospho" ester of benzoylresorcinol, 23 mole % of "diphospho" ester of benzoylresorcinol, and 2 mole % of unreacted benzoylresorcinol.

Examples 7-9

Examples 7-9 were prepared similarly according to the procedure for Example 6 except that different mole ratios of benzoylresorcinol to phosphorus oxychloride were used, as indicated in Table 4. The effect of the use of different mole ratios of benzoylresorcinol to phosphorus oxychloride on the chemical structures of phosphate esters compounds (i.e., Examples 6-9) are summarized in Table 4.

TABLE 4

|  | Ex. 6 | Ex. 7 | Ex. 8 | Ex. 9 |
|---|---|---|---|---|
| Raw Materials (Mole) | | | | |
| Benzoylresorcinol (BR) | 0.12 | 0.12 | 0.124 | 0.12 |
| Phosphorus oxychloride (POCl$_3$) | 0.051 | 0.051 | 0.04 | 0.042 |
| Triethylamine | 0.16 | 0.16 | 0.136 | 0.13 |
| BR/POCl$_3$ (mole ratio) | 2.35 | 2.35 | 3.1 | 2.86 |
| Addition Temperature (° C.) | 0–5 | 20–30 | 0–5 | 20–30 |
| Reaction Temperature (° C.) | 20–25 | 20–30 | 20–30 | 20–30 |
| Reaction Time (hour) | 3 | 3 | 3 | 3 |
| Product Weight (grams) | 26.6 | 30.0 | 29.0 | 28.9 |
| NMR Analysis Results (Mole Ratios) | | | | |
| Monophospho Ester of BR | 75 | 72 | 75 | 88 |
| Diphospho Ester of BR | 23 | 27 | 6 | 6 |
| Unreacted BR | 2 | 1 | 12 | 6 |

The reaction between benzoylresorcinol and phosphorus oxychloride was also performed in methylene chloride solvent. Experimental procedures used in the synthesis are presented in Examples 10-13.

Example 10

Phosphorus oxychloride (7.8 grams, 0.051 mole) and methylene chloride (80 mL) were charged in a 500 mL round-bottom flask with a mechanical stirrer, a thermometer, an addition funnel, and a reflux condenser with a CaCl$_2$ tube. After the contents were stirred and cooled to 0-5° C., benzoylresorcinol (22.9 grams, 0.107 mole) was added. A solution of triethylamine (15.6 grams, 0.153 mole) dissolved in methylene chloride (40 mL) was added dropwise for 1 hour at 0-5° C. The temperature was raised to 20-25° C. and held for 1 hour. The temperature was then increased to 35-40° C. and held for an additional 2 hours. The precipitate (triethylamine-HCl salts) was filtered. The filtrate was washed with water 4 times at 35° C. The resultant material (24.1 grams) was a yellow powder. A C-13 and proton NMR analysis revealed the following structures: 57 mole % of "monophospho" ester of benzoylresorcinol, 42 mole % of "diphospho" ester of benzoylresorcinol, and 1 mole % of unreacted benzoylresorcinol.

Examples 11-13

Examples 11-13 were prepared similarly according to the procedure for Example 10 except that different mole ratios of benzoylresorcinol to phosphorus oxychloride were used, as indicated in Table 5. The effect of the use of different mole ratios of benzoylresorcinol to phosphorus oxychloride on the chemical structures of phosphate esters compounds (i.e., Examples 10-13) are summarized in Table 5.

TABLE 5

|  | Ex. 10 | Ex. 11 | Ex. 12 | Ex. 13 |
|---|---|---|---|---|
| Raw Materials (mole) | | | | |
| Benzoylresorcinol (BR) | 0.107 | 0.12 | 0.12 | 0.12 |
| Phosphorus oxychloride (POCl$_3$) | 0.051 | 0.051 | 0.042 | 0.051 |
| Triethylamine | 0.153 | 0.156 | 0.13 | 0.16 |
| BR/POCl$_3$ (mole ratio) | 2.1 | 2.35 | 2.86 | 2.35 |
| Addition Temperature (° C.) | 0–5 | 0–5 | 0–5 | 0–5 |
| Reaction Temperature-1 (° C.) | 20–25 | 20–25 | 20–25 | 20–30 |
| Reaction Time-1 (hour) | 1 | 1 | 1 | 3 |
| Reaction Temperature-2 (° C.) | 35–40 | 35–40 | 35–40 | na |
| Reaction Time-2 (hour) | 2 | 2 | 2 | na |

TABLE 5-continued

|  | Ex. 10 | Ex. 11 | Ex. 12 | Ex. 13 |
|---|---|---|---|---|
| Product Weight (grams) | 24.1 | 28.5 | 28.3 | 28.4 |
| NMR Analysis Results (Mole Ratios) | | | | |
| Monophospho Ester of BR | 57 | 69 | 79 | 65 |
| Diphospho Ester of BR | 42 | 27 | 11 | 29 |
| Unreacted BR | 1 | 4 | 10 | 6 |

The structural characterization of the reaction products from the reaction between benzoylresorcinol and phosphorus oxychloride clearly showed the presence of phosphate ester and hydroxy functional groups. Compounds (2) and (3) having the structures shown in Scheme C can function both as flame retardants and UV stabilizers for polymers such as plastics and elastomers.

While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. Finally, any number disclosed herein should be construed to mean approximate, regardless of whether the word "about" or "approximately" is used in describing the number. For example, U.S. Pat. Nos. 6,784,234; 6,632,442; 6,630,524; 6,610,765; 6,552,131; 6,448,316; 6,350,804; 6,316,579; 6,204,313; 6,174,942; 6,111,016; 6,083,428; 6,075,158; 5,869,184; 5,864,004; 5,206,281; 5,204,304; and 4,246,169 disclose various compositions and methods that can be used in embodiments of the invention, with or without modifications. As such, all of the above-mentioned patents are incorporated herein by reference in their entirety.

What is claimed is:

1. A flame retardant having the formula:

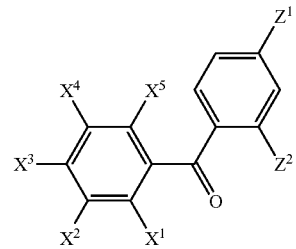

(I)

wherein each of $Z^1$ and $Z^2$ is independently a phosphate ester group;

each of $X^1$, $X^2$, $X^3$, $X^4$ and $X^5$ is independently hydrogen, halogen, nitro, cyano, acyl, alkyl, alkenyl, alkynyl, heteroalkyl, aryl, heteroaryl, cycloalkyl, or heterocycloalkyl, or $X^1$ and $X^2$, $X^2$ and $X^3$, $X^3$ and $X^4$, or $X^4$ and $X^5$ form a benzo group;

each of alkyl, alkenyl, alkynyl, heteroalkyl, aryl, heteroaryl, cycloalkyl, heterocycloalkyl or benzo is substituted or unsubstituted; and the phosphate ester group has formula (II):

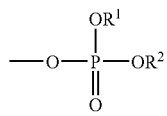

(II)

wherein each of $R^1$ and $R^2$ is independently alkyl, alkenyl, alkynyl, heteroalkyl, aryl, heteroaryl, cycloalkyl, or heterocycloalkyl; and each of alkyl, alkenyl, alkynyl, heteroalkyl, aryl, heteroaryl, cycloalkyl, and heterocycloalkyl, is substituted or unsubstituted.

2. The flame retardant of claim 1, wherein each of $X^1$, $X^2$, $X^3$, $X^4$ and $X^5$ is independently hydrogen.

3. The flame retardant of claim 1, wherein each of $X^3$, $X^4$ and $X^5$ is independently hydrogen; and $X^1$ and $X^2$ together form a benzo group.

4. The flame retardant of claim 1, wherein each of $R^1$ and $R^2$ is independently aryl.

5. The flame retardant of claim 1, wherein the phosphate ester group is selected from the group consisting of radicals having the following formulae:

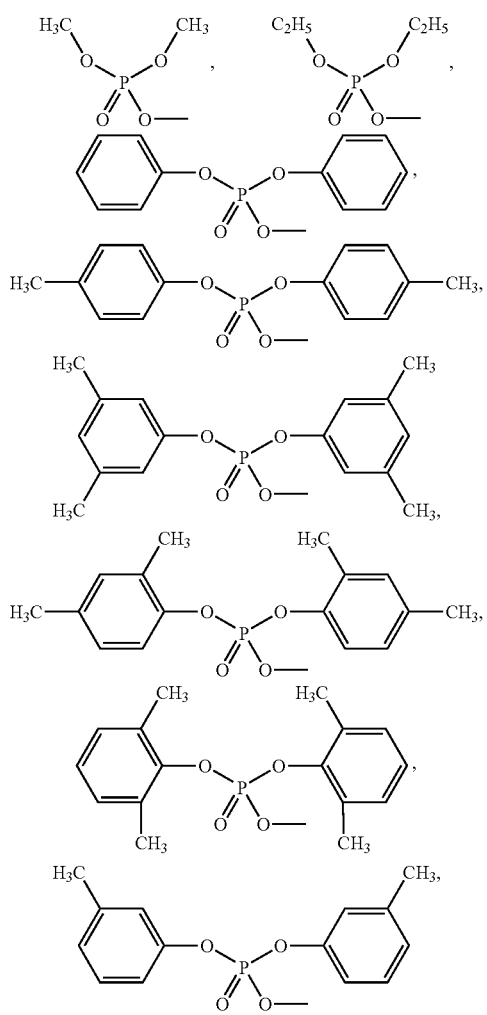

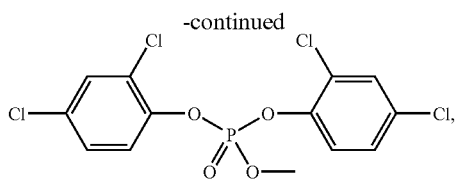

6. The flame retardant of claim 1, wherein each of $Z^1$ and $Z^2$ has the formula:

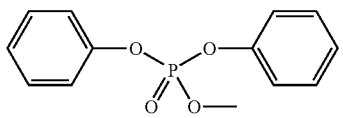

and each of $X^1$, $X^2$, $X^3$, $X^4$ and $X^5$ is independently hydrogen.

7. A process for preparing a flame retardant of claim 1 comprising the step of reacting a benzoylresorcinol compound having the formula:

(III)

with a chlorophosphate having the formula:

(IV)

in the presence of a catalyst or an acid acceptor,
wherein each of $X^1$, $X^2$, $X^3$, $X^4$ and $X^5$ is independently hydrogen, halogen, nitro, cyano, acyl, alkyl, alkenyl, alkynyl, heteroalkyl, aryl, heteroaryl, cycloalkyl, or heterocycloalkyl, or $X^1$ and $X^2$, $X^2$ and $X^3$, $X^3$ and $X^4$, or $X^4$ and $X^5$ form a benzo group and each of alkyl, alkenyl, alkynyl, heteroalkyl, aryl, heteroaryl, cycloalkyl, heterocycloalkyl or benzo is substituted or unsubstituted;

each of $R^1$ and $R^2$ is independently alkyl, alkenyl, alkynyl, heteroalkyl, aryl, heteroaryl, cycloalkyl, or heterocycloalkyl; and each of alkyl, alkenyl, alkynyl, heteroalkyl, aryl, heteroaryl, cycloalkyl, and heterocycloalkyl, is substituted or unsubstituted.

8. The process of claim 7, wherein the reaction occurs in an inert organic solvent.

9. The process of claim 8, wherein the inert organic solvent is selected from the group consisting of toluene, benzene, xylene, methylene chloride, chloroform, acetonitrile, ethers, and ketones.

10. The process of claim 7, wherein the catalyst is magnesium chloride, aluminum trichloride, titanium tetrachloride, and zinc dichloride.

11. The process of claim 10, wherein the inert organic solvent is toluene.

12. The process of claim 11, wherein the reaction temperature is greater than 100° C.

13. The process of claim 7, wherein the acid acceptor is an organic base.

14. The process of claim 13, wherein the organic base is triethylamine.

15. The process of claim 14, wherein the inert organic solvent is methylene chloride.

16. The process of claim 15, wherein the reaction temperature is lower than 35° C.

17. A flame retardant composition comprising a polymer and a flame retardant of claim 1.

18. The flame retardant composition of claim 17, wherein the polymer is selected from the group consisting of polycarbonates, poly(phenylene oxide), polyarylates, polymethacrylates, polyesters, acrylonitrile-butadiene-styrene terpolymer, high-impact polystyrene, and combinations or blends thereof.

19. The flame retardant composition of claim 17, wherein the flame retardant composition further comprises at least an additive selected from the group consisting of extenders, fibers, fillers, coupling agents, cross-linking agents, plasticizers, impact modifiers, compatibilizers, anti-blocking agents, anti-fogging agents, anti-aging agents, antioxidants, UV stabilizers, antiozonants, acid scavengers, processing aids, surfactants, lubricants, plasticizing agents, parting agents and abherents, nucleating agents, anti-static agents, slip agents, chemical blowing agents, fluorescent whitening agents, flow agents, deodorants, release agents, colorants, anti-microbials, and antidripping agents.

20. The flame retardant composition of claim 17, wherein the flame retardant composition is substantially free of a UV stabilizer.

21. An article comprising a flame retardant composition of claim 17.

22. The article of claim 21, wherein the article is selected from the group consisting of plastic products, textiles, wood and paper products, adhesives and sealants, and rubber products, aerospace parts, automotive parts, wires, cables, construction materials, materials for interiors and furnishings, appliances, electronic components, computers, and business machines.

23. The article of claim 21, wherein the polymer is selected from the group consisting of polycarbonates, poly(phenylene oxide), polyarylates, polymethacrylates, polyesters, acrylonitrile-butadiene-styrene terpolymer, high-impact polystyrene, and combinations or blends thereof.

24. The article of claim 21, wherein the flame retardant composition further comprises at least an additive selected from the group consisting of extenders, fibers, fillers, coupling agents, cross-linking agents, plasticizers, impact modifiers, compatibilizers, anti-blocking agents, anti-fogging agents, anti-aging agents, antioxidants, UV stabilizers, antiozonants, acid scavengers, processing aids, surfactants, lubricants, plasticizing agents, parting agents and abherents, nucleating agents, anti-static agents, slip agents, chemical blowing agents, fluorescent whitening agents, flow agents, deodorants, release agents, colorants, anti-microbials, and antidripping agents.

25. The article of claim 21, wherein the flame retardant composition is substantially free of a UV stabilizer.

\* \* \* \* \*

UNITED STATES PATENT AND TRADEMARK OFFICE
CERTIFICATE OF CORRECTION

PATENT NO. : 7,439,289 B2
APPLICATION NO. : 11/233537
DATED : October 21, 2008
INVENTOR(S) : Durairaj et al.

It is certified that error appears in the above-identified patent and that said Letters Patent is hereby corrected as shown below:

In column 23, line 14, delete "heterocycloalkyl," and insert -- heterocycloalkyl --.

In column 25, line 9, delete "heterocycloalkyl," and insert -- heterocycloalkyl --.

In column 25, line 19, delete "and" and insert -- or --.

In column 26, line 17, delete the second instance of the word "and".

Signed and Sealed this

Twenty-first Day of April, 2009

JOHN DOLL
*Acting Director of the United States Patent and Trademark Office*